(12) United States Patent
Shoham et al.

(10) Patent No.: US 8,518,051 B2
(45) Date of Patent: Aug. 27, 2013

(54) ROBOTIC TOTAL/PARTIAL KNEE ARTHROPLASTICS

(75) Inventors: Moshe Shoham, Hoshaya (IL); Michael Burman, Haifa (IL)

(73) Assignee: Mazor Robotics Ltd., Caesaria (IL)

( * ) Notice: Subject to any disclaimer, the term of this patent is extended or adjusted under 35 U.S.C. 154(b) by 219 days.

(21) Appl. No.: 10/557,048
(22) PCT Filed: May 16, 2004
(86) PCT No.: PCT/IL2004/000416
§ 371 (c)(1),
(2), (4) Date: Nov. 30, 2006
(87) PCT Pub. No.: WO2004/100758
PCT Pub. Date: Nov. 25, 2004

(65) Prior Publication Data
US 2007/0100258 A1 May 3, 2007

Related U.S. Application Data
(60) Provisional application No. 60/470,722, filed on May 16, 2003.

(51) Int. Cl.
| | |
|---|---|
| A61B 17/58 | (2006.01) |
| A61B 17/60 | (2006.01) |
| A61B 17/00 | (2006.01) |
| A61B 1/00 | (2006.01) |
| A61B 5/103 | (2006.01) |
| A61B 5/117 | (2006.01) |
| A61F 2/00 | (2006.01) |
| A61F 4/00 | (2006.01) |
| A61F 5/04 | (2006.01) |
| A61F 5/37 | (2006.01) |
| B23Q 16/00 | (2006.01) |
| G01B 1/00 | (2006.01) |
| G01J 1/00 | (2006.01) |
| G01N 21/00 | (2006.01) |
| G01N 23/00 | (2006.01) |

(52) U.S. Cl.
USPC .............. 606/102; 606/56; 128/882; 33/569; 33/512; 250/491.1

(58) Field of Classification Search
USPC ................ 606/79, 82, 86 R, 87, 88, 56, 102; 128/845, 882; 5/624; 269/60, 61; 74/813 R; 33/569, 512; 29/38 R, 39, 47, 48.5; 600/592; 250/491.1; 378/69
See application file for complete search history.

(56) References Cited

U.S. PATENT DOCUMENTS

| 407,481 A | * | 7/1889 | Heidenreich | ..................... 81/6 |
| 3,744,138 A | * | 7/1973 | Schuler | ........................... 33/569 |

(Continued)

FOREIGN PATENT DOCUMENTS

| EP | 1 269 924 A1 | 1/2003 |
| FR | 2 732 213 A1 | 10/1996 |

(Continued)

OTHER PUBLICATIONS

Damian McCormack, Mechanical Axis Deviation: Definitions, Measurements and Consequences, Irish Journal of Orthopaedic Surgery and Trauma, vol. 2, No. 5, http://www.iol.ie/~rcsiorth/journal/volume2/issue5/mech.htm, Aug. 30, 2000.

(Continued)

*Primary Examiner* — Kevin T Truong
*Assistant Examiner* — David Bates
(74) *Attorney, Agent, or Firm* — Daniel Feigelson

(57) ABSTRACT

A system and method for knee arthroplasty procedures, using a novel leg rotation fixture to enable the leg mechanical axis, the tibia and the femur to be mutually disposed such that the load bearing, mechanical axis of the leg runs through the center of the knee joint. A measurement gauge is provided for mounting on the tibia and for aligning a baseplate in a known position on the tibia. This baseplate supports an X-ray target plate in a known position relative to the tibia, used in determining the mechanical axis, and an optional surgical robot, used to perform tibial and femoral cuts. The position of the femur relative to the robot may be determined from X-ray imaging of the pelvic region after attachment to the baseplate of an additional target extending to the pelvic region. The system enables improvement in the accuracy of knee arthroplasty procedures.

16 Claims, 10 Drawing Sheets

(56) References Cited

U.S. PATENT DOCUMENTS

| | | | | |
|---|---|---|---|---|
| 3,764,126 | A * | 10/1973 | Arenas | 269/60 |
| 3,868,101 | A * | 2/1975 | Nozaki et al. | 269/25 |
| 4,159,658 | A * | 7/1979 | Parkinson | 74/813 L |
| 4,291,229 | A * | 9/1981 | Patt | 378/180 |
| 4,592,362 | A * | 6/1986 | Stedtfeld et al. | 378/195 |
| 4,786,063 | A * | 11/1988 | Engelhardt et al. | 279/106 |
| 4,846,452 | A * | 7/1989 | Geneczko | 269/21 |
| 4,979,949 | A * | 12/1990 | Matsen et al. | 606/53 |
| 5,372,597 | A * | 12/1994 | Hotchkiss et al. | 606/56 |
| 5,645,079 | A * | 7/1997 | Zahiri et al. | 5/610 |
| 5,690,323 | A * | 11/1997 | Puttmer et al. | 269/20 |
| 5,806,518 | A * | 9/1998 | Mittelstadt | 600/407 |
| 5,810,529 | A * | 9/1998 | Morz | 409/222 |
| 6,096,082 | A * | 8/2000 | Stegmuller et al. | 623/20.15 |
| 6,712,824 | B2 | 3/2004 | Millard et al. | |
| 7,154,243 | B2 * | 12/2006 | Weiss | 318/560 |
| 8,104,377 | B2 * | 1/2012 | Nakamura | 74/813 R |
| 2003/0149429 | A1 * | 8/2003 | Ferrante et al. | 606/59 |
| 2011/0272872 | A1 * | 11/2011 | Stadtfeld | 269/61 |

FOREIGN PATENT DOCUMENTS

| | | |
|---|---|---|
| WO | 00/54687 A1 | 9/2000 |
| WO | WO 03105659 A2 * | 12/2003 |

OTHER PUBLICATIONS

PCT International Search Report and Written Opinion of the ISA in WO 2004/100758, to Mazor Surgical Technologies Ltd., issued on Feb. 10, 2005.

European Examination Report in EP Application No. 04 733 268, to Mazor Surgical Technologies Ltd., issued on Apr. 4, 2011.

Supplementary European Search Report in EP Application No. 04 733 268, to Mazor Surgical Technologies Ltd., published Dec. 20, 2010.

"Preservation—minimally invasive unicompartmental knee system", DePuy International Ltd of Leeds, UK, 2007.

M.Jakopec et al, "The Acrobot® System for Total Knee Replacement", Industrial Robot, vol. 30, No. 11, pp. 61-66, 2003.

* cited by examiner

ROBOTIC TOTAL/PARTIAL KNEE ARTHROPLASTICS

FIELD OF THE INVENTION

The present invention relates to the field of the use of robotic systems in knee joint replacement operations, and especially for improving the accuracy of implant installation and their longevity using a novel orthopedic guidance system.

BACKGROUND OF THE INVENTION

The goals of the operative procedures known as total knee replacement, partial knee arthroplastic or the uni-condyler procedure (TKR/TKA/UNI) are to restore pain free walking capability in patients having worn or diseased knee joints. In these common orthopedic procedures, damaged surfaces of the knee bones are replaced with prosthetic joint implants, installed at the distal femoral and proximal tibial bone ends, after appropriate cuts of the tibia and femur bones have been made by the surgeon. In order to ensure correct functionality of the knee and a long working life of the implants, all of the implanted components must be positioned with high precision in relation to the mechanical axis of the leg, the anatomical axes of the bones and the mating surfaces between the bones and the prostheses.

A number of geometric anatomical relationships must be fulfilled for the reconstructed knee to function correctly and with longevity. These relationships can be observed by reference to FIG. 1, which is a schematic illustration of the optimal anatomic position of the bones of the leg, as viewed from the anterior/posterior (A/P) direction. The relationships are as follows:
  (a) The mechanical axis of the leg 10, running from the center of the acetabulum head 20 of the femur to the center of the ankle 22, should pass through the defined middle of the knee joint 12.
  (b) The femur anatomical axis 14 should be inclined at an angle of about 7° with the leg mechanical axis. This angle is known as the valgus angle 16.
  (c) The tibia bone axis 18 should be collinear with the mechanical axis 10 of the leg.
  (d) The mechanical axis of the leg, the axis of the femur bone and the axis of the tibia bone should lie in one plane, when the leg is completely straightened. This plane is that of the plane of the drawing of FIG. 1.

When accurately performed, the procedure should arrange the entire knee joint so that forces are transferred through the component parts of the leg along a well-defined mechanical axis of the leg, from the center of the acetabulum head 20, through the middle of the knee joint 12, and to the ankle 22.

In order to satisfy all these requirements, the surgeon must be able to fulfil a number of conditions with respect to the correct orientation of the planes cut at the ends of the bones for the installation of the implants:
  (i) Control of the orientation of the cutting planes relatively to the mechanical axis of the leg.
  (ii) Control of the orientation of the tibial cutting plane.
  (iii) Control of the orientation of the femoral cutting plane.

With prior art techniques as currently used, measurements of the leg mechanical axis are not performed intraoperatively. Generally the surgeon performs a visual estimation of the required cuts, relying on his senses and experience, or is assisted in this task by the use of mechanical rods laid along the estimated axes of the bones. This task is problematic because of the difficulty of accurately estimating the orientation of the cutting planes, each having two rotational degrees of freedom, relative to the leg's mechanical axis, the tibia axis and the femur axis, and one translational degree of freedom relative to the bone positions, in a situation when almost all of the leg structure is covered by soft tissue and no axis measurements are performed. In a typical procedure, a complete X-ray image of the leg is used to enable the surgeon to estimate the 7° valgus angle, which is the angle with the perpendicular to the femur axis at which the cut of the end of the femur is made.

The instrumentation currently available can generally give an indication only of large errors in such a cutting plane orientation. Thus, although the simple implantation guidance instrumentation currently used, such as direction gauges and mechanical guide rods attached to the leg, is of some assistance to the surgeon in achieving the correct alignment of the leg axis and the implants, the success thereof depends very largely on the surgeon's experience. According to studies such as that reported in "Our Experiences with Robot Assisted Surgery in Comparison with Navigation and Manual Technique in Total Knee Arthroplasty", by S. Mai, et al., Computer Assisted Orthopedic Surgery, 2002, and that reported in "Acrobot system for total knee replacement" by M. Jakopec, et al., published in Industrial Robot, Vol. 30, No. 11, pp. 61-66, 2003, over one third of such operations were found to have deviations from ideal prosthesis alignment which resulted in premature failure of the repaired joint. It is known that there is a high correlation between survival rate of the implant, and misalignment thereof. According to other studies, it is believed that the failure rate of such knee joint operations, as defined by the need for a corrective operation within 2 years, is up to 15% of the total number performed, half of which are due to misalignment problems. Because of the complexity of the situation produced, a corrective operation is often several times more costly than a regular operation. The main reasons for such high misalignment rates is that the current instrumentation usage depends highly on the surgeon's experience.

Many different approaches have been proposed in order to reduce the failure rate in this field of orthopedics. Navigation systems have been proposed, both with or without CT correlation. These systems are variously based on CT scans, fiducial marks, the matching of bone surfaces with template bones, and x-ray imaging, together with state-of-the-art cutting tools and the use of instruments such as robots. One such prior art system uses tracker markers on the upper leg, which are followed by the navigational system as the leg is swung, the center of motion of these markers defining the center of the hip joint. The same procedure performed with tracking markers on the lower leg enables the center of the knee joint to be determined by the navigation system, since the tibia revolves in an arc with the center of the knee joint at its center. The ankle is then designated with a touch pointer to enable the tibia axis to be defined. Finally, the cutting jigs mounted on the bones are also provided with tracking markers to define their position to the navigator system. This system thus is able to define the axes of the bones, their joint centers and the position at which the cut is to be made using the cut guidance jig. The main drawback of such systems is their complexity, the longer procedure time required, their price and their large size, all or some of which may be contributory factors as to why there has so far been small usage of such systems in these procedures, when compared to the use of conventional TKA tools.

There therefore exists a need for a new system, method and associated accessories for enabling the performance of TKR/TKA/UNI procedures to be executed with higher precision and success rate than those currently used, and with less dependence on the professional subjective skills and judgement of the surgeon performing the procedure.

The disclosures of each of the publications mentioned in this section and in other sections of the specification, are hereby incorporated by reference, each in its entirety.

SUMMARY OF THE INVENTION

The present invention seeks to provide a new system, method and associated accessories, which enable an increase in the accuracy of TKR/TKA/UNI procedures to be achieved, and, by the use of automating the procedure, relieves the onus of the measurements from the surgeon, without the need for the addition of a complex and costly navigation system. The system and procedure of the present invention allows for optimum implant positioning. The system preferably uses a robotic system to define the cutting planes, and an adjustable leg rotation fixture to determine of the mechanical axis of the leg. The novel adjustable leg rotation fixture of the present invention can also be used advantageously in the standard manual cut operations, where conventional cut guidance jigs are used instead of a robot.

There is therefore provided, according to a first preferred embodiment of the present invention, a system for aiding the performance of knee joint replacement operations, in which the mechanical axis of the leg is first determined by use of an adjustable leg rotation fixture, which is affixed to the operating table and is clamped around the leg, enabling the leg to rotate about its axis. By this means the mechanical axis of the leg can be defined and motion of the leg limited to rotation about this axis.

According to a further preferred embodiment of the present invention, a baseplate is provided, which is affixed to the tibia by means of a gauge device, and on which baseplate is mounted a small surgical robot in a position and orientation known relative to the tibia bone geometry. On the baseplate can also be mounted a target plate, whose position can be readily determined in X-ray images taken of the area using a C-arm. Using X-ray images taken with the leg in at least two different rotated positions, preferably at up to 90° to each other, the location of the mechanical axis of the leg can be obtained in the coordinate system of the C-arm. This is a particular important advantage of the present system, unattainable in such a simple manner in prior art systems.

The position of the tibia axis is determined, according to a further preferred embodiment of the present invention, by the use of a marker line attached to the gauge device, and aligned with the tibia axis by means of X-ray imaging. Once the tibia axis and the leg mechanical axis are both known in the C-arm coordinate system by means of the target projections in the X-ray images, and hence are also known relative to the baseplate position of the robot, the robot can be mounted on the baseplate and used either to align the fixture used by the surgeon to guide the saw accurately for the desired tibia cut, or the saw can be mounted directly on the robot, and the tibia cut performed by the robot itself.

Once the tibia cut has been performed, the femur cut has to be performed at the correct orientation and at the correct distance from the tibia cut. This position can be obtained using the system of the present invention, according to a first preferred embodiment, by providing an additional degree of freedom to the above-described leg rotation fixture of the present invention, to enable the leg to perform a rotation in the plane of the operating table, thus enabling by means of at least one further C-arm X-ray image, to determine the coordinates of the center of the femur head at the center of rotation of the leg axis. According to a second preferred method, a target rod is attached in a known position onto the base plate, and extending from the knee region along the femur. Its presence in a further C-arm image taken at the pelvic region, enables the femur mechanical axis to be defined, since the center of the femur head can be obtained by image processing of the top of the femur, and the presence of the target rod in this image enables the position of the base plate to be related thereto, and the position of the base plate is known relative to the C-arm coordinate system. Once the femur mechanical axis is known in addition to the leg mechanical axis in the C-arm coordinate system, the robot can be used to define the position of the femur cut, in a similar way to that performed for the tibia cut. The system allows choice of the cut angle and distance relative to the tibia cut.

The system and its associated accessories thus enables both the tibia and femur cuts to be achieved with robotic accuracy, at positions and orientations chosen by the surgeon to match the availability of implant sizes.

The potential advantages engendered by the use of the system of the present invention, over currently used procedures, include:

(1) Improved accuracy of the procedure, resulting from accurate guidance for the surgeon and reliable measurements and instrumentation.
(2) Minimal invasiveness of procedure due to accurate instrumentation guidance.
(3) Simplification of the work flow of the entire procedure.
(4) Enabling the surgeon to easily modify the cutting planes of the bones.
(5) Shortening of the procedure time.
(6) Fewer surgical instruments required for the procedure.
(7) Decreased bone damage.

Additionally, the system allows the surgeon:

(8) To choose the bone cutting planes in relation to the mechanical axis of the leg, which cannot be measured and related to intraoperatively using prior art procedures.
(9) To perform the cuts accurately by use of robot-held jigs that guide the surgical tools, or by allowing the robot to perform the cut directly.
(10) To have a high degree of flexibility for jig relocation, if mandated by an intraoperative decision of the surgeon, which is not available in prior art procedures, where a change in decision about the cutting plane involves relocation of the cutting jig on the bone.

There is thus provided in accordance with a preferred embodiment of the present invention, a system for determining the mechanical axis of a leg of a subject, comprising a support ring, the support ring being adapted to rotate at least about an axis perpendicular to its plane, the support ring having an adjustable clamping device adapted to hold the leg within the support ring in such a position that rotation of the support ring about its axis rotates the leg about its mechanical axis. The system preferably also comprises a base element to which the ring is attached by means of a bearing, the bearing allowing the ring to rotate, but fixing its spatial position relative to the base element. Furthermore, a pointer is preferably attached to the support ring, the pointer being aimed at the axis of rotation of the support ring, and the subject's leg is preferably positioned such that the pointer points to the center of the ankle of the subject.

In accordance with still another preferred embodiment of the present invention, there is provided a system as described above and also comprising an X-ray identifiable target plate adapted to be fixed to a bone of the leg, such that at least the orientation of the leg can be determined by X-ray imaging of the bone. The X-ray imaging is preferably performed at two angles of rotation of the leg about its mechanical axis, and the X-ray imaging is performed by means of an X-ray imaging system having a coordinate system, such that the mechanical axis of the leg is defined in the coordinate system.

Any of the above described systems, also comprise a cutting tool whose alignment is known relative to the bone, such that the cutting tool can cut the bone at a predetermined plane relative to the mechanical axis of the leg. The alignment of the cutting tool relative to the bone is known preferably by means of attachment to the bone of a cutting jig for the cutting tool.

In accordance with still another preferred embodiment of the present invention, the alignment of the cutting tool relative to the bone is preferably accomplished by means of a robot mounted in a known position relative to the bone, such that the predetermined plane can be adjusted at least by means of programmed motion of the robot.

There is also provided in accordance with yet a further preferred embodiment of the present invention, a system for performing a cut on a bone of a subject at a predetermined plane on the bone, comprising:
(i) a baseplate adapted to be fixed to the bone, such that the location and orientation of the baseplate is fixed relative to the bone,
(ii) an X-ray identifiable target plate adapted to be fixed to the baseplate, such that a first set of information regarding at least one of the location and orientation of the bone can be determined by X-ray imaging of the bone,
(iii) an X-ray identifiable feature at least two points along the length of the bone, such that a second set of information about the axis of the bone is determined by X-ray imaging of the bone, and
(iv) a cutting guide disposed at a predetermined location relative to the baseplate, the location being determined from at least one of the first and second sets of information, such that the cut is made on the bone at the predetermined plane.

In the above described system, the X-ray identifiable feature may preferably be a guide rod aligned along the length of the bone generally parallel to the axis of the bone, or it may be the image of the bone itself, such that the axis of the bone is discerned. Furthermore, the system may also preferably comprise a gauge element having at least one reference point in contact with at least one feature of the bone, such that the position of the above-mentioned baseplate can be fixed relative to the at least one feature of the bone. The gauge element also preferably comprises a shaft section such that the gauge can be aligned along the length of the bone.

Any of these above-mentioned preferred embodiments of this system for performing a cut on a bone of a subject may also preferably comprise a robot attached to the baseplate, such that the position of the robot is known relative to the bone. In such a case, the cutting guide can preferably be mounted on the robot, such that the predetermined plane on the bone can be reached by at least one programmed position of the robot. In all of the above described systems, the bone may preferably be a tibia.

There is even further provided in accordance with a preferred embodiment of the present invention, a system for determining the mechanical axis of a femur, comprising:
(i) an X-ray identifiable target adapted to be fixed in a predefined position close to the knee joint region of the femur, the target extending to the head of the femur in the pelvic region of the leg,
(ii) an X-ray imager generating at least one image of the pelvic region, such that the target in the pelvic region is defined in the coordinate system of the X-ray imager, and at least one image of the knee region showing the target, such that the head of the femur and the knee region are both correlated to the coordinate system of the X-ray imager, and
(iii) an image processor for determining the center of the femoral head from at least one X-ray image of the pelvic region, such that the mechanical axis of the femur is determined between the center of the femoral head and the center of the knee joint.

Furthermore, in accordance with yet another preferred embodiment of the present invention, there is provided a system for determining the mechanical axis of a femur of a subject on an operating table, comprising:
(i) a leg holding fixture, having a plane of translation in the plane of the operating table such that the leg rotates about its femoral head center in the plane of the operating table, and
(ii) an X-ray imager generating (a) at least two images of the femoral head center at different rotational positions of the leg such that the femoral head center coordinates are determined at the center of rotation of the leg, and (b) at least one image of the knee joint of the subject such that the center of the knee joint is determined,
wherein the mechanical axis of the femur is determined by the space line between the center of the femoral head and the center of the knee joint.

There is also provided in accordance with a further preferred embodiment of the present invention, a system for preparing a knee joint of a leg of a subject for implant insertion, the leg comprising tibia and femur bones, comprising:
(i) an X-ray imager for imaging the leg, the X-ray imager having a coordinate system,
(ii) a leg rotational fixture for determining the mechanical axis of the leg in the coordinate system of the X-ray imager,
(iii) a baseplate adapted to be fixed to the tibia in the region of the knee joint such that the baseplate is defined in the coordinate system of the X-ray imager,
(iv) an X-ray identifiable target plate adapted to be fixed to the baseplate, and an X-ray identifiable feature at least two points along the length of the tibia, such that the axis of the tibia is defined in the coordinate system of the X-ray imager,
(v) a femur mechanical axis determiner, utilizing at least one X-ray image of the head of the femur, and at least one X-ray image of the region of the knee joint to determine the femur mechanical axis in the coordinate system of the X-ray imager,
(vi) a controller for calculating desired cutting planes of the tibia and the femur such that when the knee joint is assembled, the tibia axis, the femur mechanical axis and the leg mechanical axis are aligned in a predetermined manner, and
(vii) a cutting tool disposed relative to the baseplate such that the cutting plane of the cutting tool is defined in the coordinate system of the X-ray imager, such that the ends of the tibia and the femur are cut in the desired planes.

In the above described system, the femur mechanical axis determiner preferably comprises an X-ray identifiable target adapted to be fixed in a predefined position close to the knee joint region of the femur, the target extending to the head of the femur in the pelvic region of the leg, such that the at least one image of the pelvic region and the at least one image of the knee region both show the target correlated to the coordinate system of the X-ray imager, and an image processor for determining the center of the femoral head from the at least one X-ray image of the pelvic region, such that the mechanical axis of the femur is determined between the center of the femoral head and the center of the knee joint.

Alternatively and preferably, the subject is disposed on an operating table, and the femur mechanical axis determiner then comprises a leg holding fixture, having a plane of translation in the plane of the operating table such that the leg rotates about its femoral head center in the plane of the operating table, such that the at least one image of the pelvic region comprises at least two images of the femoral head center at different rotational positions of the leg such that the femoral head center coordinates are determined at the center of rotation of the leg, such that the mechanical axis of the femur is determined by the space line between the center of the femoral head and the center of the knee joint.

In accordance with yet another preferred embodiment of the present invention, there is provided a method of preparing for implant insertion in a knee joint of a leg of a subject, the leg comprising tibia and femur bones, comprising the steps of:

(i) providing an X-ray imager for imaging the leg, the X-ray imager having a coordinate system,
(ii) defining the mechanical axis of the leg in the coordinate system of the X-ray imager,
(iii) defining the tibia axis in the coordinate system of the X-ray imager,
(iv) defining the femur mechanical axis in the coordinate system of the X-ray imager,
(v) disposing a baseplate on the tibia in the region of the knee joint such that the baseplate is defined in the coordinate system of the X-ray imager,
(vi) calculating desired cutting planes of the tibia and the femur such that when the knee joint is assembled, the tibia axis, the femur mechanical axis and the leg mechanical axis are aligned in a predetermined manner,
(vii) disposing a cutting tool relative to the baseplate such that the cutting plane of the cutting tool is defined in the coordinate system of the X-ray imager, and
(viii) cutting the ends of the tibia and the femur in the desired planes.

In the above described method, the predetermined manner is preferably such that the femur mechanical axis and the leg mechanical axis are essentially collinear. Additionally, the step of aligning the femur mechanical axis and the leg mechanical axis essentially collinear may preferably be achieved by laterally cutting an end of the femur at essentially the valgus angle to a plane perpendicular to the anatomical axis of the femur. According to this method, the step of cutting is preferably such that the leg mechanical axis and the anatomical axis of the femur are aligned at essentially the valgus angle when the knee joint is assembled.

In accordance with still another preferred embodiment of the present invention, in the above described method, the step of defining the tibia axis may preferably be performed by means of an X-ray identifiable guide line aligned along the tibia, and the step of defining the mechanical axis of the leg may preferably be performed by inserting the leg when straightened into a leg rotational fixture and X-ray imaging at least two rotational orientations of the leg.

There is further provided in accordance with still another preferred embodiment of the present invention, the above described method, and wherein the step of defining the femur mechanical axis is performed by the steps of:

(i) translating the leg rotational fixture in the plane of the operating table such that the leg rotates about its femoral head center in the plane of the operating table,
(ii) determining the femoral head center coordinates at the center of rotation of the leg, by means of X-ray imaging of the pelvic region of at least two different rotational positions of the leg,
(iii) determining the coordinates of the center of the knee joint by X-ray imaging of the knee joint, and
(iv) defining the femur mechanical axis between the center of the femoral head and the center of the knee joint.

Alternatively and preferably, the step of defining the femur mechanical axis is performed by the steps of:

(i) attaching a known target in a predefined position to the base, the target extending to the head of the femur in the pelvic region of the leg,
(ii) X-ray imaging the pelvic region, such that the target in the pelvic region is defined in the coordinate system of the X-ray imager,
(iii) correlating the X-ray imaging of the pelvic region with the X-ray imaging of the base, such that the head of the femur and the base are correlated to the same coordinate system of the X-ray imager,
(iv) determining the center of the femoral head by image processing of an X-ray of the pelvic region, and
(v) determining the center of the knee joint by X-ray imaging of the knee joint, and
(vi) defining the femur mechanical axis between the center of the femoral head and the center of the knee joint.

Alternatively and preferably, the step of defining the femur mechanical axis may be performed by extracting data on the anatomical location of parts of the femur by inspection of X-ray images of the leg.

Any of the above-described methods may preferably also comprise the step of mounting a surgical robot onto the base, such that the robot position is known in the coordinate system of the X-ray imager, and wherein the step of cutting the ends of the tibia and the femur is performed by means of a cutting tool operating in a cutting jig mounted on the robot. In this case, the robot may preferably be moved such that the cutting is performed in the desired planes by means of at least one programmed step, determined in the step of calculating the desired cutting planes. Furthermore, according to another preferred embodiment, the robot is preferably moved such that the cutting is performed in the desired planes, by means of at least one manual input by the surgeon to desired cutting planes determined by the surgeon from information provided by the X-ray imager.

BRIEF DESCRIPTION OF THE DRAWINGS

The present invention will be understood and appreciated more fully from the following detailed description, taken in conjunction with the drawings in which:

FIG. 12A is an A/P image, and FIG. 12B a lateral image.

DETAILED DESCRIPTION OF PREFERRED EMBODIMENTS

Figure 1:
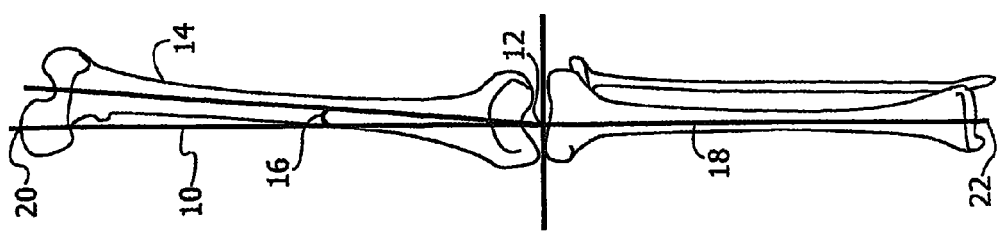
FIG. 1 illustrates schematically an anterior/posterior (A/P) view of the bones of a leg, showing the various axes of the leg components in their optimal anatomical positions.

Reference is now made to FIG. 1, which illustrates schematically an anterior/posterior (A/P) view of the bones of a leg, showing the various axes of the leg components in their correct anatomical positions, as used by the system and methods of the present invention in the execution of the surgical procedures enabled thereby. The details of the parts of FIG. 1 have been described hereinabove in the Background to the Invention section of this application.

As a first step, the surgeon performs the conventional antero-lateral or antero-medial skin incision of the knee. He then makes a cut along the Retinaculum pattelae mediale in order to move aside the patella and to expose the entire structure of the knee joint, including the top end of the tibia, the bottom end of the femur, the meniscus, ligaments, etc., as is known in routine orthopedic surgical procedures on the knee. Standard surgical instruments are used to pull aside the patella together with the Retinaculum pattelae mediale. Such a cut does not change the relative bone positions, since the Retinaculum pattelae mediale does not influence the relative position of the tibia and the femur. After removal of the Corpus adiposum infrapattelare, the surgeon has access to the area of the Facies articularis superior, which is the upper surface of the tibia, and which is to be cut at the correct angle to receive the tibia implant.

Figure 2B:
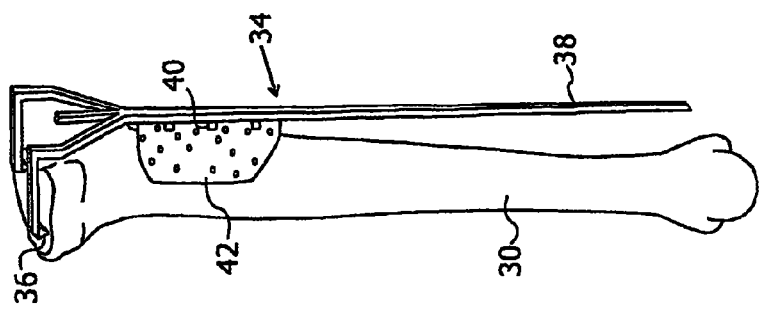
FIGS. 2A and 2B are schematic views of a tibia bone showing the Facies articularis superior and a measurement gauge, constructed and operative according to a preferred embodiment of the present invention is aligned along the tibia.
Figure 2A:
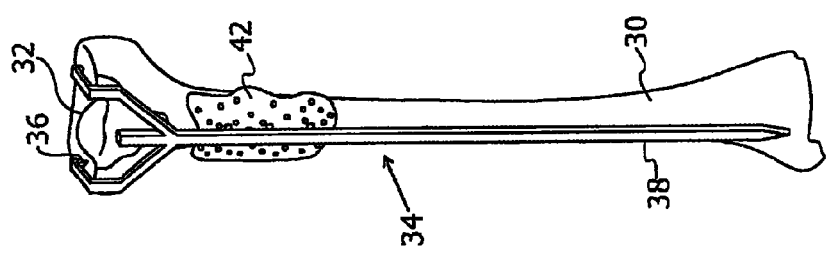
Figure 8:
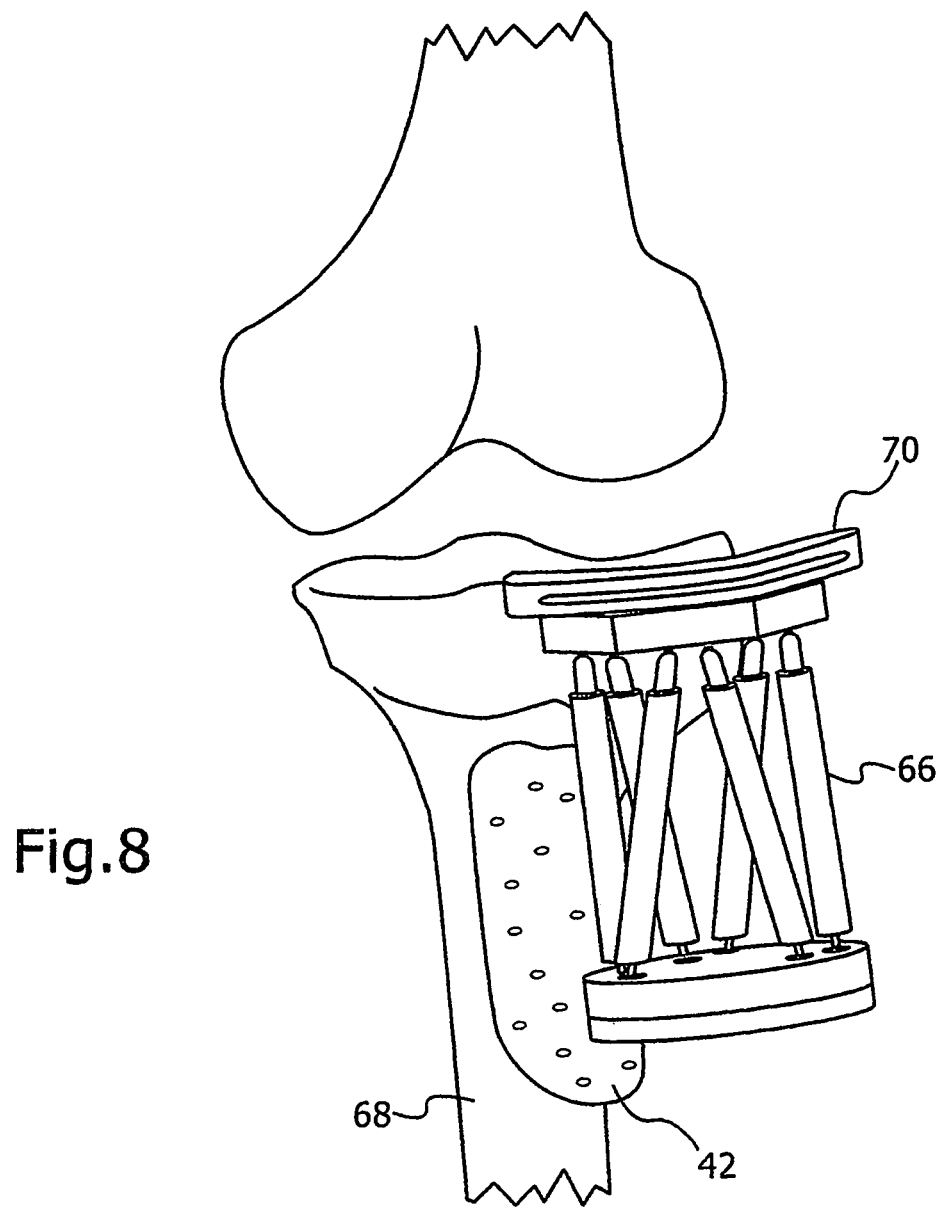
FIG. 8 is a schematic illustration of a miniature surgical robot attached to the base plate on the tibia bone in position for the surgeon to perform a tibia cut, according to a further preferred embodiment of the present invention.

Reference is now made to FIGS. 2A and 2B which are schematic views of a tibia bone 30, showing the Facies articularis superior 32. A measurement gauge 34, constructed and operative according to a preferred embodiment of the present invention, is aligned along the tibia. This measurement gauge is used to define the position and location of instruments and accessories used to operate on the tibia, with reference to the position of the plane of the Facies articularis superior 32. The position of the measurement gauge with respect to the plane of the Facies articularis superior, may preferably be defined by means of reference tongues 36 in contact with the upper surfaces of the tibia, while the shank 38 of the measurement gauge is directed down the length of the tibia to define the axis of the tibia. Near its top end, the measurement gauge 34 preferably has reference pins 40 which define the position by which a base plate 42 is attached to the tibia near its top end, at a known location and orientation relative to the Facies articularis superior. This base plate can be used for three main functions: (i) for mounting a target plate, visible in X-ray images taken of the region, such that its position and hence the position of the tibia is definable from such X-ray images, (ii) for mounting a small surgical robot in a predefined position and orientation relative to the tibia top surface, and by means of which the cutting jig is aligned for performing the cut at the top of the tibia as close as possible to the desired final position and orientation of the cutting plane, and (iii) for mounting a conventional cutting guide for performing manual cutting, the guide preferably being aligned and fixed according to fixing pins having known positions on the base plate. Alternatively and preferably, when a robot is used, a cutting tool, such as a milling head may be attached directly to the robot, instead of the use of cutting jigs held on the robot. The robotic system may preferably be of the type produced by Mazor Surgical Technologies Ltd., of Caesaria, Israel, assignee of the present application, and as illustrated in FIG. 8 hereinbelow, though it is to be understood that the invention is not meant to be limited to use of that particular robotic system and is also executable using other robotic systems, or even manual cutting jig systems. The base plate is preferably attached with three pins to the tibia, (not visible in FIGS. 2A and 2B) and which hold it rigidly relative to the tibia bone. Since the base plate is fixed by these pins directly into the tibia, there is no interaction between the base plate and the soft tissues of the leg of the patient, and its position, and the position of the robot mounted thereon are thus defined relative to the upper surfaces of the tibia.

Figure 3:
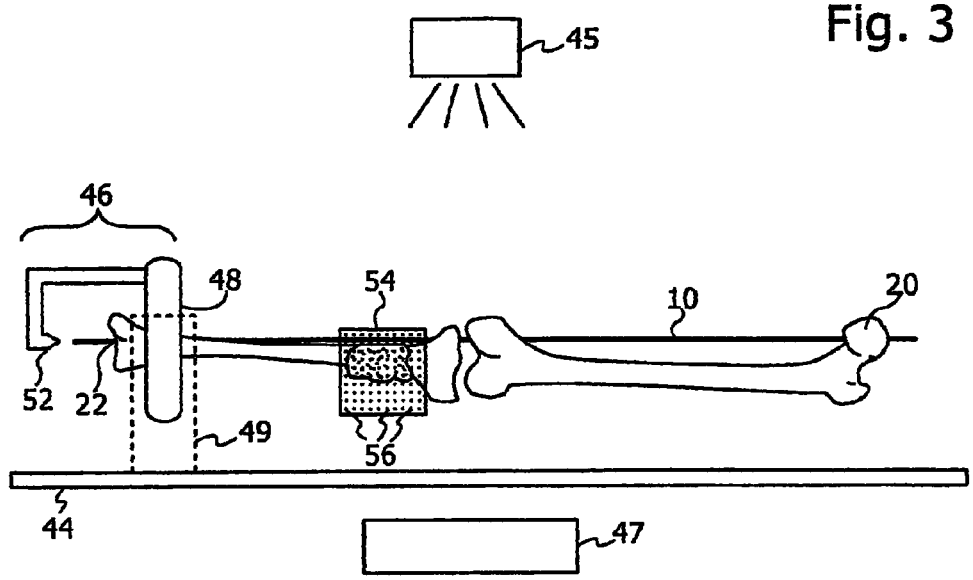
FIG. 3 is a schematic view of a complete system for defining the cutting planes of the tibia and femur of a subject's leg, such that optimum TKR/TKA/UNI procedures can be performed, and including an X-ray imager, image processing and system controller, and a leg rotation fixture, all constructed and operative according to further preferred embodiments of the present invention.
Figure 4:
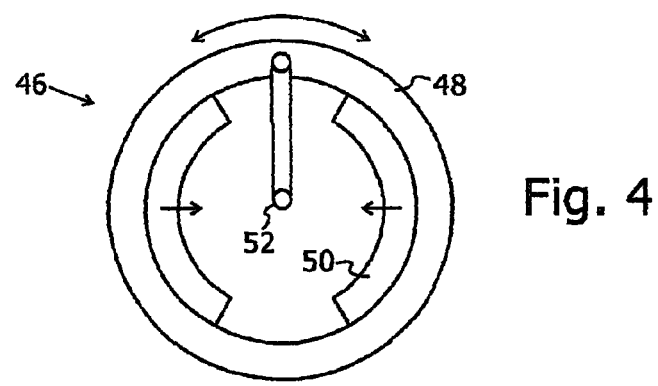
FIG. 4 is a cross sectional view of the leg rotation fixture of FIG. 3.
Figure 5:
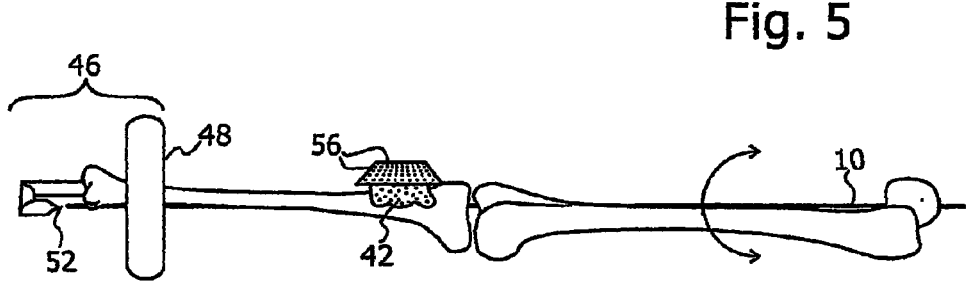
FIG. 5 schematically shows a leg mounted in the leg rotation fixture of FIGS. 3 and 4, after executing a rotation, to illustrate how the fixture limits motion of the leg to rotation about the mechanical axis.

Once the position of the base plate is known with respect to the tibia, the positions of the target plate and the robot and its cutting jig or sawing/milling head are also known. It is then necessary to define the position of the mechanical axis of the leg which is the first of the axes of which, a knowledge of their positions are essential for accurate execution of the procedure. Reference is now made to FIGS. 3 to 5, which illustrate schematically a leg rotation fixture, constructed and operative according to a further preferred embodiment of the present invention, and whose function is for defining the mechanical axis of the leg. Such a leg rotation fixture is part of a complete system for defining the cutting planes of the tibia and femur of a subject's leg, such that optimum TKR/TKA/UNI procedures can be performed.

Reference is first made to FIG. 3, which is a schematic view of the bones of the leg of a subject lying on an operating table 44, equipped with a conventional X-ray imaging system 45, 47, such as a C-arm, including a control system 47 analyzing the data contained in the X-ray images to determine such parameters as the axes of the component tibia and femur bones of the leg, and the mechanical axis of the leg itself and providing therefrom, control signals to direct the robot to place cutting jigs, or to perform the cuts, as described in the specific sections hereinbelow.

The bottom of the leg of the subject is mounted in the leg rotation fixture 46. The leg rotating device preferably has the shape of a ring 48, which is locked onto the leg at the commencement of the procedure. This ring is preferably supported in a base element 49 attached to the operating table. Reference is now made to FIG. 4 which is an end view of the leg rotation fixture 46, showing a set of adjustable jaws 50 which are closed onto the patient's leg to lock the ring 48 onto the leg. The ring is preferably supported in its base element by means of a self-aligning spherical bearing which allows the ring to move in all three axis of rotations relative to the operating table, such that it can rotate freely especially about the axis running perpendicular to the plane of the ring. The purpose of the fixture, when operated in conjunction with the hip joint, is to restrict the leg movement of the patient in all directions except one, a rotation about the mechanical axis of the leg. The leg rotation fixture ring is attached to the leg by means of its jaws, preferably at the lower end of tibia just above the ankle, such as at the Facies articularis inferior. The leg rotation fixture also has a pointer device 52 attached to the ring, and aligned at the center of rotation of the fixture. Before closing the clamping jaws, the position of the leg is adjusted until the pointer device points to the center of the ankle, such that it is known that the center of the ankle is at the center of rotation of the fixture. When the leg has been so restricted in the ring, the only movement that it can make is thus a rotation about the axis which passes through the center 20 of the femoral head and the center 22 of the ankle. This axis is, by definition, the mechanical axis 10 of the leg. FIG. 5 shows the leg mounted in the leg rotation fixture, after executing a rotation of about 90°, to illustrate how the fixture limits motion of the leg to rotation about the mechanical axis. In FIGS. 3 and 5 are also shown the base plate 42 affixed to the tibia, and an X-ray target device in the form of a target plate 54 fixed to the base plate 42. The function of this target plate 54 is now explained.

Figure 6A:
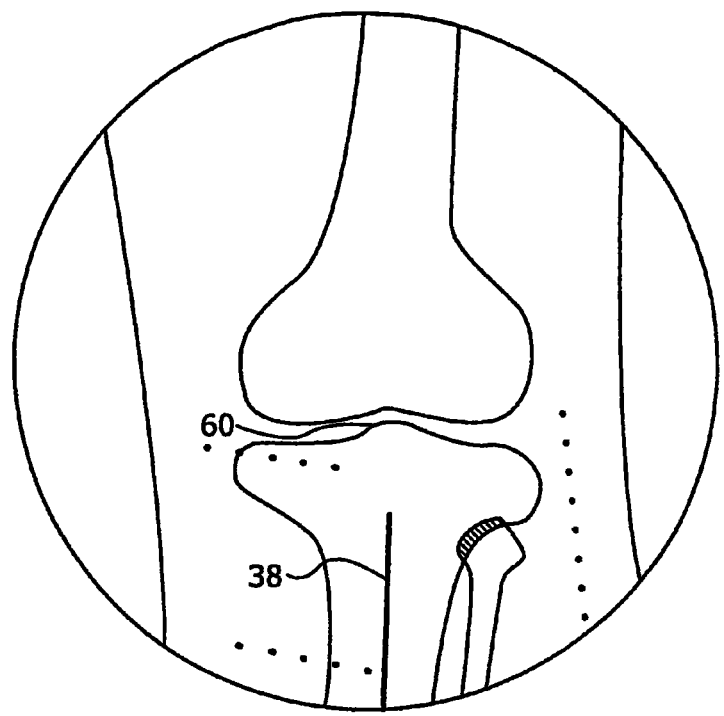
FIGS. 6A and 6B are schematic reproductions of examples of two X-ray projections in two different orientations of the leg in the leg rotation fixture, taken intraoperatively using the C-arm.
Figure 6B:
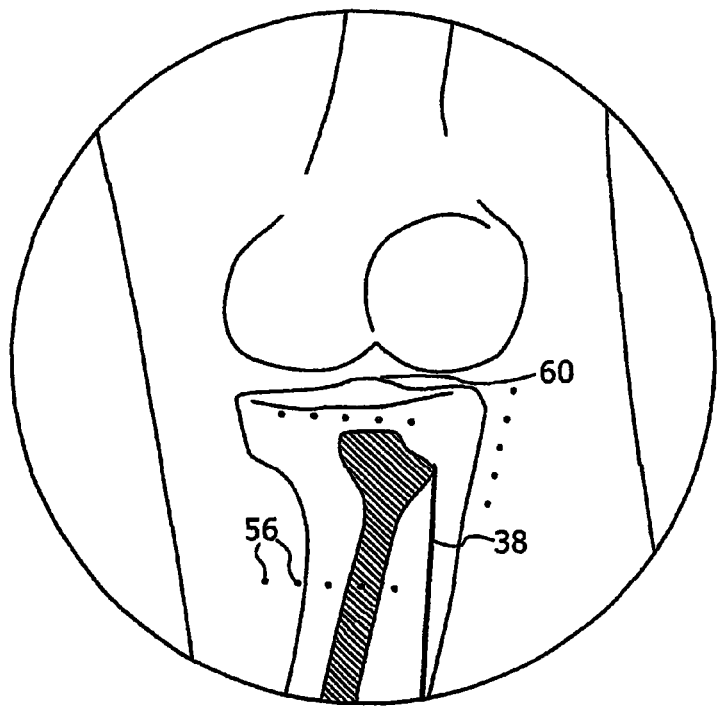

In order to link the mechanical axis of the leg, as defined by the rotational axis of the leg rotation fixture, to the anatomical position of the bones of the patient, X-ray images are required. At least two X-ray projections in two different orientations of the leg are preferably taken. Reference is now made to FIGS. 6A and 6B, which are schematic reproductions of examples of two such images, taken intraoperatively using the C-arm, with the leg at two positions, mutually rotated at about 90° from each other. FIG. 6A is close to an A/P image, and FIG. 6B is taken at an appreciable rotational angle to that of FIG. 6A, and is close to a lateral image. The target device 54 is attached to the base plate 42, as shown in FIGS. 3 and 5, and thus moves with rotation of the leg. The target device 54 is constructed in such a way that its position and orientation relative to the X-ray source can be determined from the projected image of the marker balls 56 within the target plate. Since the target and the leg move together as one rigid body, once the rotation axis of the target 54 is determined from these two images, that axis is also the rotation axis of the leg, namely, the mechanical axis. In order to obtain accurate results, the X-ray source distortions have to be calibrated and compensated for using a calibration system and software, as is known in the art.

The procedure by which the target positions in the X-ray images are analyzed in order to determine the position of the mechanical axis directly on the X-ray images of the leg is now explained, according to the following steps:

1. Firstly, the position of the target must be determined in both images. Since the rotation of the target is around one defined axis, namely the leg's mechanical axis, it is possible to utilize simple geometrical calculations on the target in order to achieve rapid and accurate recognition and definition of the coordinate system of the target in the C-arm coordinate system (C.S.), as follows:
(a) From each of the two x-ray images, 4×4 homogeneous transformation matrices $^{C\text{-}arm}T_{Im1}$ and $^{C\text{-}arm}T_{Im2}$, are calculated, where $$^{C\text{-}arm}T_{im} = \begin{bmatrix} R_{3\times3} & d_{3\times1} \\ 0 \quad 0 \quad 0 & 1 \end{bmatrix} \quad (1)$$

$^{C\text{-}arm}T_{Im1}$ is a transformation matrix from the target C.S. to the C-arm C.S. in the first X-ray image.
$^{C\text{-}arm}T_{Im2}$ is a transformation matrix from the target C.S. to the C-arm C.S. in the second X-ray image.
R is an orthonormal matrix, which describes the orientation of the target in the C-arm C.S.
d is the position of the origin of the target in the C-arm C.S.

2. From these transformation matrices $^{C\text{-}arm}T_{Im1}$ and $^{C\text{-}arm}T_{Im2}$ and assuming that the C-arm C.S. is a real-world C.S., used as a static reference frame for all other C.S's, a clear transformation $^{im2}T_{im1}$ can be defined from the target C.S. in the first X-ray image to the target C.S. in the second X-ray image.

$$I = {}^{C\text{-}arm}T_{im1}{}^{-1} \, {}^{im2}T_{im1} \, {}^{C\text{-}arm}T_{im2} \quad (2)$$

$$^{im1}T_{im2} = {}^{C\text{-}arm}T_{im1} \, {}^{C\text{-}arm}T_{im2}{}^{-1} \quad (3)$$

3. From $^{im2}T_{im1}$, the direction n̂ of the mechanical axis of the leg and the amount of rotation θ between the images can be calculated.

4. From these calculated values of rotation and location of the target origin in both x-ray images, the location of the mechanical axis in the C-arm C.S. can be obtained.

5. That information can thus be presented directly on the X-ray images for the surgeon's validation. The projection of the leg mechanical axis onto the X-ray images can greatly assist the surgeon in making decisions about the optimal position and orientation of the bone cuts. This information is useful for providing the surgeon with information also for manual cutting procedures.

6. Furthermore, since the exact orientation of the target relative to the mechanical axis of the leg is known, then when the robot is attached to its locating pins on the base plate, its position relative to the mechanical axis is also well defined and known. The robot could thus be brought into a position such that any accessory attached to its operating workholder, such as a saw guiding jig, could also be brought to a position to be perpendicular to the mechanical axis of the leg, or if so programmed, to be at any desired inclination to the perpendicular to the mechanical axis.

7. Therefore, at this point of the procedure, the plane of saw cuts executed using the robot, relative to the mechanical axis of the leg, is known, and could be aligned either perpendicular to the mechanical axis, or at any other chosen angle to the axis.

Figure 7A:
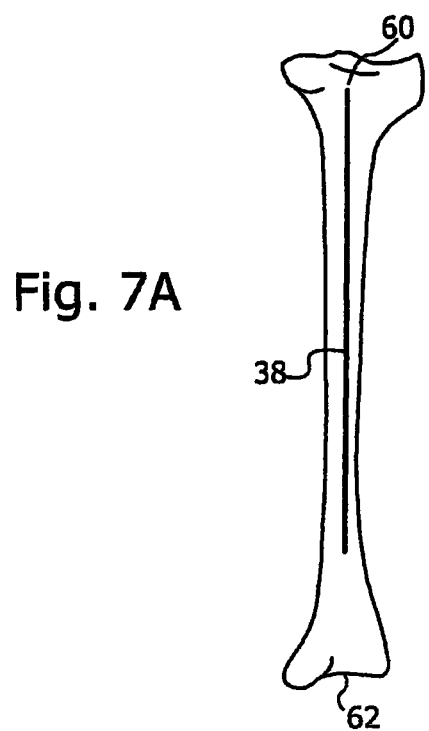
FIGS. 7A and 7B which are schematic X-ray images which illustrate the use of the gauge shown in FIGS. 2A and 2B, for determining the location of the tibia axis.
Figure 7B:
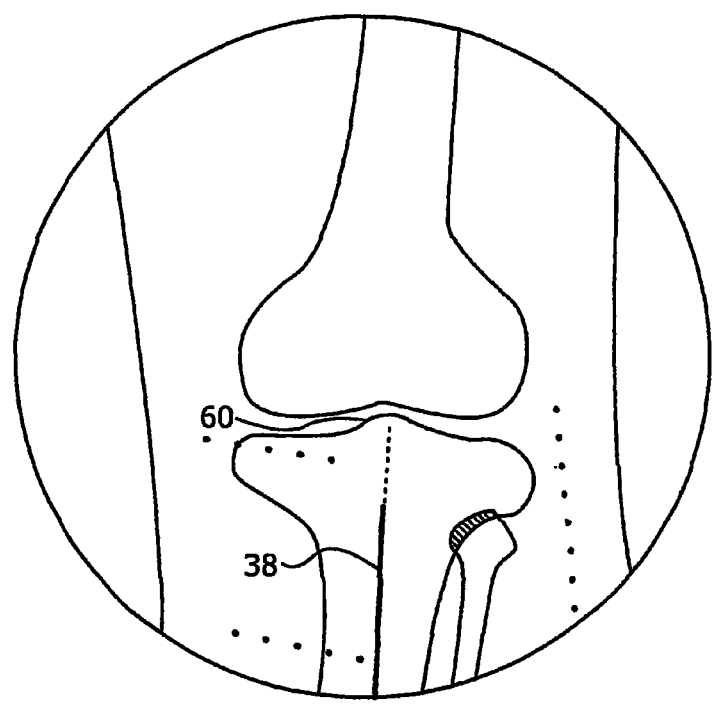

8. However, in order to correctly perform cuts in the tibia bone, it is also necessary to know the location of the tibia axis, running from the middle of the knee joint, the Eminetia intercondylaris, to the ankle. Reference is now made to FIGS. 7A and 7B which illustrate schematically how this procedure is performed, using the gauge 34 shown in FIGS. 2A and 2B, that was used to locate the base plate on the tibia. However, for the current step, as is seen in FIG. 7A, the shaft 38 of the gauge is positioned in such a way that it points from the Eminetia intercondylaris 60 to the center of the ankle 62, which is also located at the center of the ring. The position of the Eminetia intercondylaris 60, and the way in which the marker shaft 38 points exactly at this position, is clearly seen in the X-ray image of the knee shown in FIG. 7B.

9. In order to find the axis of the tibia bone, one of the X-ray images has to such that the projection of the marker shaft is coincident with the axis of the tibia. This is easily achieved for an X-ray image taken in the anterior/posterior (AP) direction relative to the tibia.
10. In an alternative procedure for finding the tibia axis, the surgeon marks the Eminetia intercondylaris 60 in both of the X-ray images, using an interactive touch screen. This procedure is simple and accurate and can be illustrated in the X-ray images previously shown in FIGS. 6A and 6B. From the points marked by the surgeon, the location of a point 60, placed on the Eminetia intercondylaris, can be readily calculated in 3D space in the C-arm C.S. When combined with information about the projection of the tibia axis in one of the x-ray images, the exact location and orientation of the tibia bone axis can be calculated in the C-arm C.S.
11. At this point in the procedure, the information so far known about the spatial location and orientation of the various bones and worktools comprises:
   (a) Location and orientation of the target and hence the robot in the C-arm C.S.
   (b) Location and orientation of the leg mechanical axis in the C-arm C.S.
   (c) Location and orientation of the tibia axis in the C-arm C.S.
12. At this point of the procedure, the surgeon is now able to perform the cut of the tibia bone, at the correct orientation and position relative to the mechanical axis of the leg and to the tibia axis. The target plate can thus be removed from the base plate, and the robot attached in its place. Reference is now made to FIG. 8, which is a schematic illustration of a miniature surgical robot 66 attached to the base plate 42 on the tibia bone 68 in position for the surgeon to perform a tibia cut. The robot is preferably a miniature parallel robot, such as manufactured by Mazor Surgical Technologies Ltd. A cutting jig 70 is mounted on the workpiece holder of the robot, and is used by the surgeon to provide accurate guidance for his saw blade when cutting the tibia itself. Alternatively and preferably, a cutting tool can be mounted on the robot workpiece holder, and the cutting performed by the robot itself Alternatively and preferably, manual cutting guide jigs can be mounted on the base plate, and manual cutting performed.
13. The angle of the cut can be varied by programming the robot to tilt to provide the desired posterior slope angle for tibia cut, and the robot brings the cutting jig accurately to the desired orientation. In this manner, the cut can be correctly aligned to ensure correct fit and orientation of the implants available for the operation.

The above operation procedure flow provides the surgeon with good system flexibility, in the following ways:
(a) The surgeon can insert data into the program and the robot will bring the cutting jig to the exact desired position. The accuracy is limited only by the accuracy of the X-ray imaging performed, and the calculations performed thereon.
(b) The surgeon has the ability to easily correct the cutting system position, if, based on his knowledge and experience, the calculated position and orientation are not optimal. This can be done by simple data insertion into the robot control program, and there is no need to realign the cutting jig manually.
(c) The surgeon can manipulate the robot in a manual mode by means of a joystick, thereby constraining the robotic system to a different set of cutting conditions, for instance, the relocation of the cutting plane while maintaining the angle of posterior slope constant with respect to mechanical axis.
(d) The robot position and cutting plane orientation can be projected onto the X-ray images during the robot manipulation in order to validate system movements and to give the surgeon a real-time indication about the cuts being performed.

From this point on, the surgeon could feasibly continue with the methods of the conventional technology and instruments, based on the assumption that the first performed cut of the tibia is in the correct position and orientation. By this is meant the alignment of the femur cut at the valgus angle to the tibia cut, and at the desired distance form the tibia cut. However, if this were to be done, then one of the primary goals described in the Background to the Invention section of this application, namely the cutting the femur bone according to the correct mechanical axis alignment, would not be achieved. In order to achieve this objective, it is necessary to positively identify the location and orientation of the mechanical axis of the femur bone. Consequently, according to additional preferred embodiments of the methods and apparatus of the present invention, the following additional steps are necessary in order to achieve optimal benefit from this invention.

14. In order to obtain the desired alignment of the femoral cut relative to the already cut tibia bone, the surgeon now has to take into consideration the following issues:
   (i) The cut has to be oriented correctly relative to the femur axis.
   (ii) The cut has to be correctly aligned relative to the plane of the tibia bone cut in order to obtain the correct alignment relative to the leg mechanical axis.
   (iii) The gap between the cut planes on the tibia and femur has to suit available implant sizes. This ensures correct ligament balancing in the repaired knee. It is preferable to make the bone cut gap from the outset to match the available sizes of existing implants, rather than to force the surgeon to find the closest available implants to fit an existing gap, with the possible resultant complications of loosening of the joint, or of an over-tight joint.

Using current techniques, these tasks are problematic, requiring from the surgeons a high degree of professional training and judgement. Unfortunately, there are many cases when those tasks cannot be completed as successfully as would be desired.

Figure 9A:
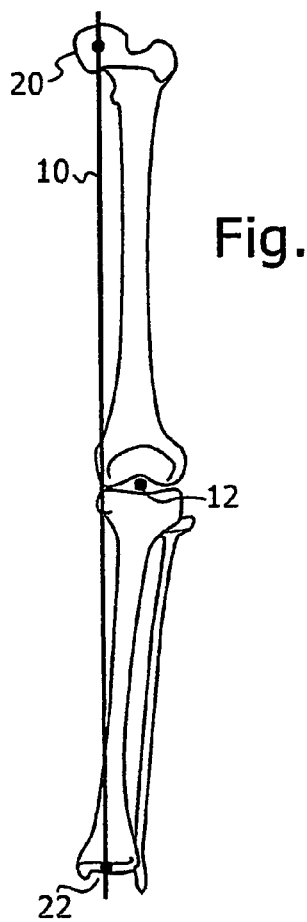
FIGS. 9A and 9B are schematic drawings showing the leg bones of a subject, before and after knee replacement surgery also designed to bring the femoral bone axis to a valgus angle of about 7° with the leg mechanical axis, as enabled by the methods and apparatus of the present invention.
Figure 9B:
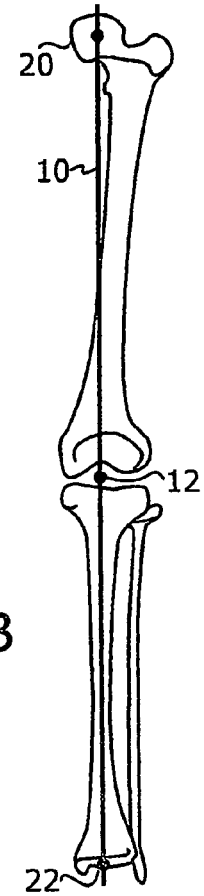

15. The femur cut can be made either at the chosen valgus angle to the tibia cut, as is done in currently used TKR procedures, or parallel to the tibia cut, in what is known as the Preservation procedure, as described in an explanation brochure entitled "Preservation—minimally invasive unicompartmental knee system", published by DePuy International Ltd. of Leeds, U.K.
16. The femoral cut should be carried out in such a way that the Fossa intercondylaris, which is the hollow in the center of the end of the femur between the Condylus medialis and the Condylus lateralis, lies on the leg mechanical axis. This brings the femoral bone axis to a valgus angle of about 7° with the leg mechanical axis. This procedure is illustrated by reference to FIGS. 9A and 9B. In FIG. 9A is shown schematically, a leg in which the desired axis orientation is not present. Thus, the leg mechanical axis 10, which is the load bearing axis running from the center of the acetabulum head 20 down to the center of the ankle 22, does not pass through the Fossa intercondylaris 12, at the center of the knee joint. When the femoral cut is carried out at the correct desired angle, according to preferred methods and using the preferred apparatus of the present invention, then the resulting alignment of the femur and tibia should be as shown in FIG. 9B, where it is seen that the mechanical axis 10 now passes through the center of the knee joint 12, as desired. In many cases, using current techniques, this task cannot be accomplished intra-operatively due to the absence of suitable measurement means.

According to further preferred embodiments of the present invention, a number of different solutions are proposed for solving the issue of the definition of the anatomical femur axis, which is readily visible and definable in X-ray images of the region, and the mechanical femur axis, or the space line. The mechanical femur axis or the space line is the line joining the center of femur head, the caput femoris, and the Fossa intercondylaris of the femur.

According to a first preferred embodiment, an amended leg rotation fixture is used, having an additional planar degree of freedom, allowing the patient's leg to perform movement in the plane of the operating table. By means of a further C-arm X-ray image, taken at the pelvic end of the femur, it is possible to locate in the C-arm C.S., the coordinates of the center of the femur head, caput femoris, as this is the center of rotation of the femur. This is similar to the technique described above for determining the leg mechanical axis using the target device. From the coordinates of the center of the femur head, and from the previous calculation of the location of the Fossa intercondylaris of the femur which is assumed to be very close to the calculated position of the Eminentia intercondylaris described above in relation to FIGS. 7A and 7B, the coordinates of the space line which connects these two points can be calculated.

Figure 10:
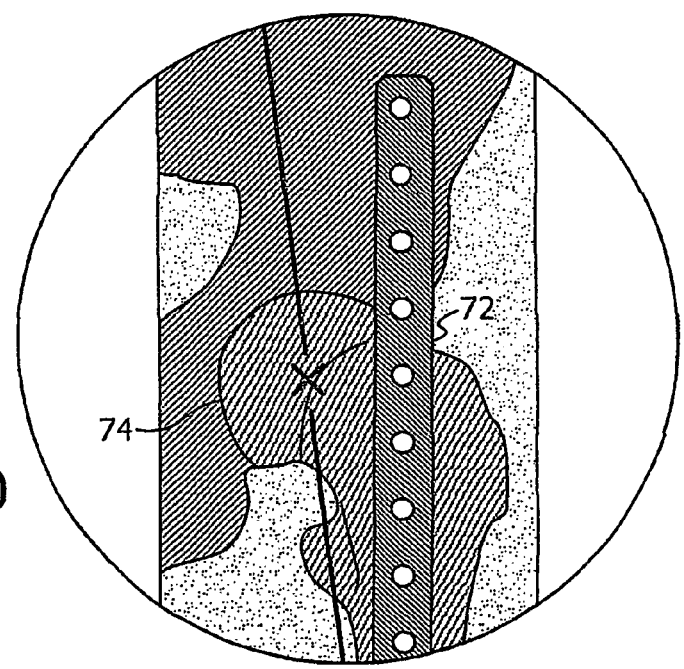
FIG. 10 illustrates schematically an X-ray image of the pelvic joint with the femur head, showing how the femur mechanical axis is determined according to one preferred embodiment of the present invention.

Reference is now made to FIG. 10, which illustrates schematically an X-ray image of the pelvic joint with the femur head. This figure is used to illustrate a second preferred embodiment, in which a special designed target device 72, about 50 cm long, is attached to the upper leg, from the knee region and terminating in the pelvic region. After taking images of the knee region, the C-arm device has to be relocated along the patient's leg towards the pelvis to take the image shown in FIG. 10. It is assumed that during this translation movement, the C-arm undergoes only small orientation changes, such that the orientation of the projection plane can be considered not to have changed, and the X-ray image can still be considered to have a similar orientation to the previous images taken of the knee region. Since the target is present in all of these views, the details on the pelvic region image can be easily related to the coordinate systems of the two previous images. The femur head 74 can be identified by standard image processing, and its center, marked with a X in FIG. 9, can also be readily defined by image processing techniques. Since from the knee region images, the position of the Fossa intercondylaris is known relative to the target 72, correlation of the knee and pelvic region images allows the determination of the desired mechanical femur axis or space line.

Figure 11A:
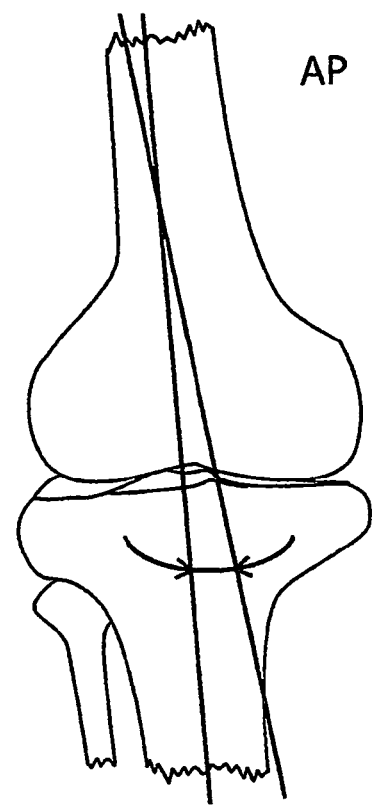
FIGS. 11A and 11B are an example of a pair of preoperative X-ray images of a knee joint, FIG. 11A being an A/P image, and FIG. 11B a lateral image, as used for determining the femur mechanical axis according to another preferred embodiment of the present invention.
Figure 11B:
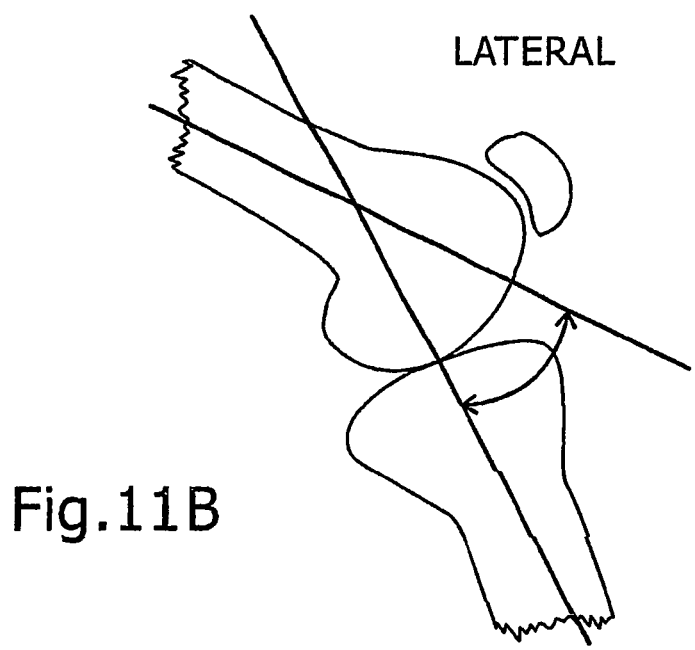

According to a third preferred embodiment, before the operation, the surgeon makes a study of the x-ray images (AP and lateral) of the patient's knee joints as the patient's leg is straightened. This is a prescribed standard procedure before any such knee operation. Measurements instruments are available, such as the lined slides for knee damage measurement supplied by DePuy International Ltd., for making measurements of the angles between the tibia axis and the femur axis in two planes—AP and lateral. Reference is now made to FIGS. 11A and 11B, which show an example of a pair of such preoperative X-ray images of a knee joint, FIG. 11A being an A/P image, and FIG. 11B a lateral image.

Assuming that the relative state of the bones, as captured on these images, would be the situation at the time of the operation, and assuming that correct angle measurements with good accuracy have been performed, the surgeon loads that data into the robot control software. After processing of the data, both bone axes can be projected onto X-ray images, taken during the operation.

17. By any of the above described methods, or by any other suitable known method, the femur mechanical axis or the space line are thus defined in the C-arm C.S., and hence also in the robot C.S. The tibia axis and the leg mechanical axis have also been defined previously in the robot C.S. As a result, the control system now has information which enables it to know where each bone is located, where the desired location of each bone is, and where the robot itself is located, relative to those bones. Once all of this spatial information has been defined and loaded into the system, the femur cut can be performed. At this stage, the leg is preferably removed from the leg rotation fixture, since the knee joint may need to be bent during subsequent operational steps, or even to perform the cut. Once the leg has been removed, the location of the cutting tool is known only relative to the base plate on the tibia. Therefore, a method must be used to relate the cutting tool to the femur data also. Four preferred methods of performing this are proposed. According to a first method, the leg is simply held in a straight position while the femur cut is being performed, such that the original location of the femur relative to the tibia is maintained. According to a second preferred method, predefined spacer jigs, such as are known in the art, are used to physically define the position of the femur relative to the tibia. According to a third preferred method, the calculated data is input to the robot to align a cutting jig, which is then affixed to the femur. Using this jig, the desired cutting position on the femur is known regardless of how the knee is subsequently bent. According to a fourth preferred method, the calculated data is used to define a mounting position of the robot on the femur, and the robot is removed from the tibia baseplate, and is mounted directly on the femur, such that the cut can be performed using the robot itself either directly or by positioning a cutting guidance jig on the femur. Since there are a number of methods of performing the femur cut itself, four of which are suggested above, the steps described in the following paragraphs may be relevant only for one or more of the methods, and are thus meant to be accordingly understood.

18. Since the system has no acquired information about bone damage extent, and how much bone has to be removed, the surgeon can mark the desired cut depth level on the X-ray images or even bring the robot manually to the desired cutting depth, such as by use of a joystick controller.

Figure 12A:
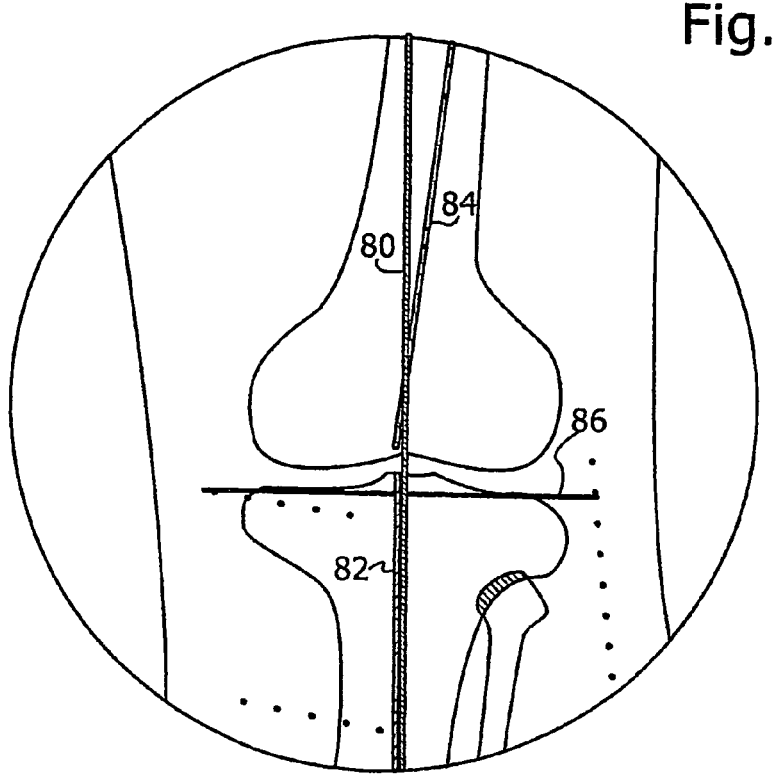
FIGS. 12A and 12B are schematic examples of projections of cutting plane information onto X-ray images for the surgeon's review, according to further preferred embodiments of the present invention, where
Figure 12B:
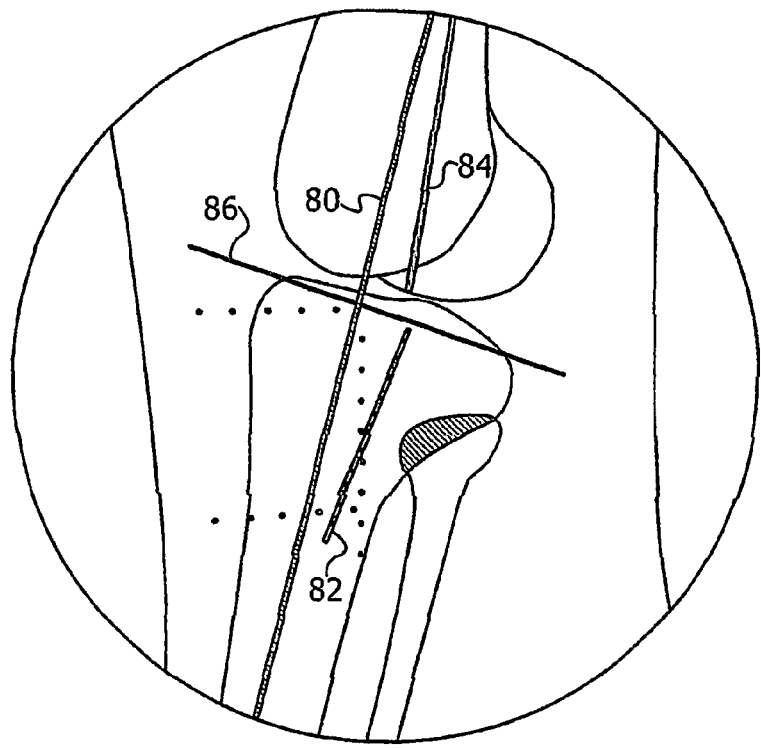

19. The system advises the surgeon about all the cutting planes angles and projects them onto the x-ray images for surgeon verification. FIGS. 12A (A/P) and 12B (lateral) are schematic examples of such projection of information onto X-ray images for the surgeon's review. In FIGS. 12A and 12B are shown the leg mechanical axis 80, the tibia axis 82, and the femur axis 84, as well as a line 86 to represent the surgically desired cutting plane of the tibia. Once the surgeon has verified the data on the X-ray images, the system sends the robot to the correct location for guiding the surgical tool or for executing of the cuts themselves. The cutting planes shown on the femur are generally only used in this step if the femur cut is performed with the leg still in the rotation fixture, or with the leg straightened after removal from the leg rotation fixture.

20. In order to make a femur cut in those configurations when the robot is attached to the tibia, a special jig is preferably attached to the robot to stabilize its position relative to the femur during the cutting process itself. This is necessary since the robot is attached to the tibia bone, and the tibia bone is not rigidly attached to the femur. Attachment of that special jig to the femur, is necessary in order to provide good dimensional stability between the robot and the femur bone. This jig attachment is a standard task, which is also performed in current procedures.

21. In those cases when the surgeon decides not to correct bone angles, a single jig for cutting both bones can be used, for those preferred embodiments where the mutual location of the femur and tibia are known. The planes of such a jig would have a related orientation, which would include the posterior tibia slope.

22. After the tibia and the femur cuts have been accurately performed in the planned location, the surgeon can proceed with the fitting of the implants using the standard instruments and procedures available.

Figure 13A:
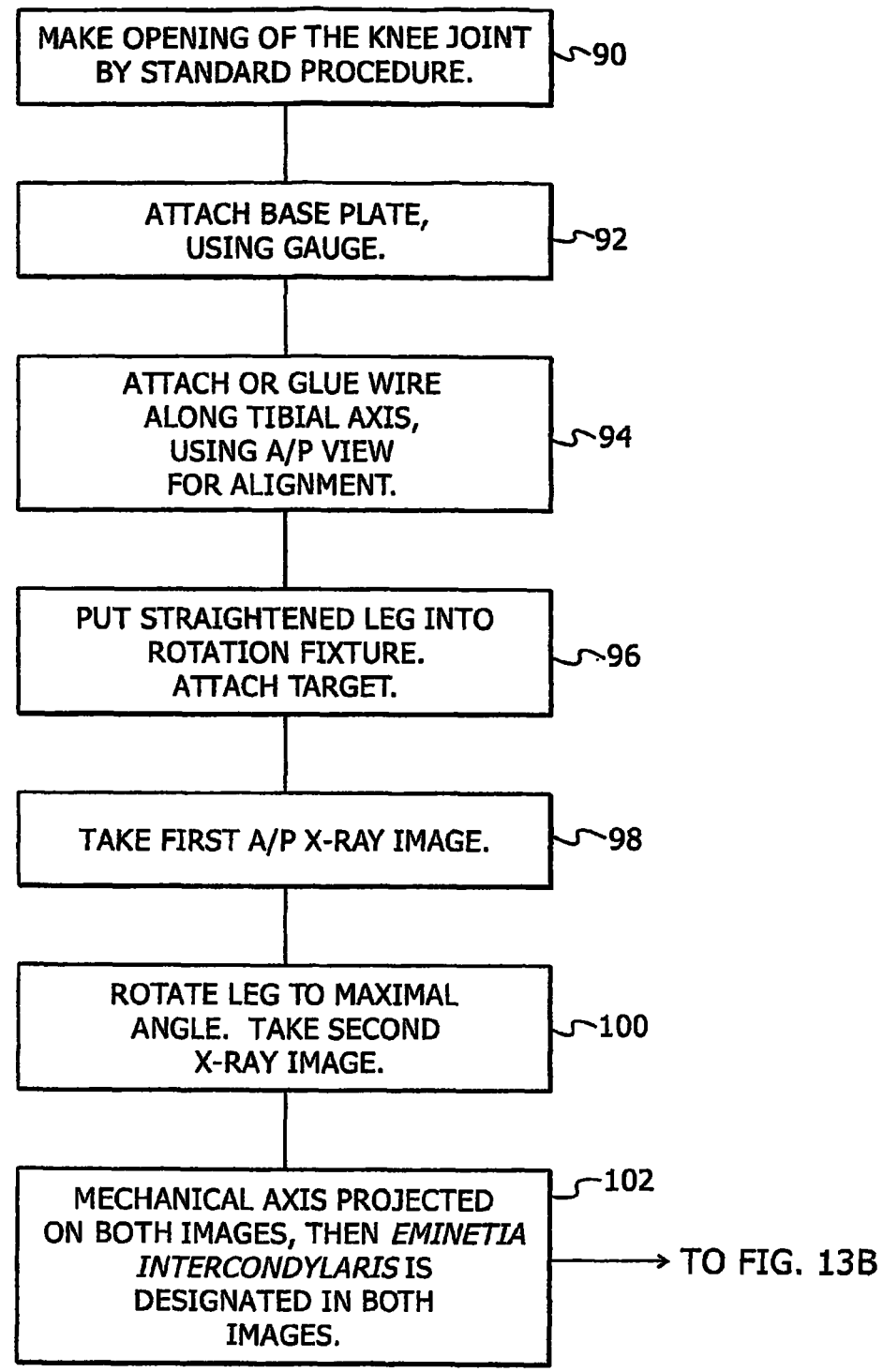
FIGS. 13A and 13B illustrate a complete procedure for performing knee replacement operations using the processes and apparatus according to further preferred embodiments of the present invention.
Figure 13B:
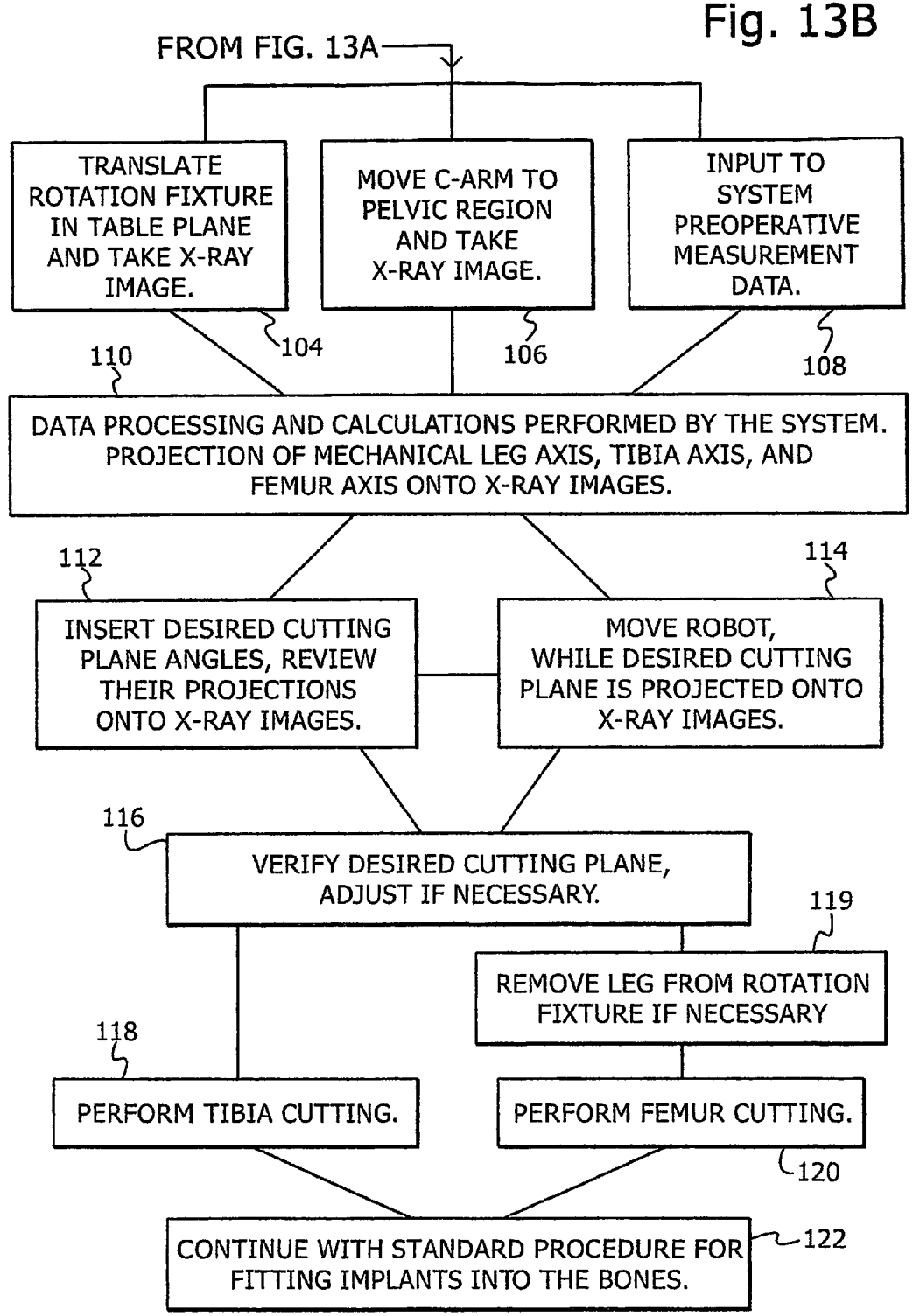

Reference is now made to the flow chart in FIGS. 13A and 13B, which illustrates a preferred complete procedure for performing knee replacement operations using the procedures of the present invention. The various steps shown in FIGS. 13A and 13B generally follow the procedure described in the Detailed Description section of this application, as applicable for the robotic cutting embodiments described therein. Furthermore, at some of the steps where a number of alternatives are possible, the chart does not always present all of the possible combinations or their order, where the order may be optionally changed. This is particularly so for the latter stages of the method, where a number of options are open for performing the cuts themselves.

It is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A system for determining the mechanical axis of a leg of a subject, said mechanical axis running from the femoral head to the center of the ankle joint of said leg, and said system comprising:
    a leg rotation fixture, comprising:
        a peripheral support frame, said peripheral support frame comprising an adjustable clamping device attached thereto, such that when the subject's leg is inserted through said peripheral support frame, actuation of said clamping device clamps the leg therewithin;
        a bearing which enables said leg rotation fixture to rotate about an axis perpendicular to the plane of its peripheral support frame; and
        a pointer attached to said peripheral support frame in such a position that it is aimed at said axis about which said leg rotation fixture rotates,
    wherein said adjustable clamping device is spatially adjustable to a position in said peripheral support frame such that said pointer can be aimed at the center of the ankle of the subject, such that rotation of said leg rotation fixture about said axis rotates said leg about its mechanical axis.

2. A system according to claim 1 and also comprising an X-ray identifiable target plate adapted to be fixed to a bone of said leg, such that at least the orientation of said leg can be determined by X-ray imaging of said bone.

3. A system according to claim 2 and wherein said X-ray imaging is performed at two angles of rotation of said leg about its mechanical axis.

4. A system according to claim 3 and wherein said X-ray imaging is performed by means of an X-ray imaging system and said mechanical axis of said leg is defined in the X-ray imaging system coordinate system.

5. A system according to claim 2 and also comprising a cutting tool whose alignment is known relative to said bone, such that said cutting tool can cut said bone at a predetermined position relative to said mechanical axis of said leg.

6. A system according to claim 5 and wherein said alignment of said cutting tool relative to said bone is known by means of attachment to said bone of a cutting jig for said cutting tool.

7. A system according to claim 5 and wherein said alignment of said cutting tool relative to said bone is accomplished by a robot mounted in a known position relative to said bone, such that said predetermined position can be adjusted at least by means of programmed motion of said robot.

8. A system according to claim 1 wherein said leg rotation fixture is attached to an operating table, such that when the subject is on said operating table, said leg rotation fixture restricts movement of the leg to rotation about the mechanical axis of the leg.

9. A system for determining the mechanical axis of a leg of a subject, said mechanical axis running from the femoral head to the center of the ankle joint of said leg, and said system comprising:
    a leg rotation fixture, comprising:
        a peripheral support frame, said peripheral support frame comprising an integrally attached adjustable clamping device, such that when the subject's leg is inserted through said peripheral support frame, actuation of said clamping device clamps the leg therewithin;
        a bearing which enables said leg rotation fixture to rotate about an axis perpendicular to the plane of its peripheral support frame; and
        a pointer attached to said peripheral support frame in such a position that it is aimed at said axis about which said leg rotation fixture rotates,
    wherein said adjustable clamping device is spatially adjustable to a position in said peripheral support frame such that said pointer can be aimed at the center of the ankle of the subject, such that said rotation axis is aligned with the mechanical axis of the leg.

10. A system according to claim 9, further comprising an X-ray identifiable target plate adapted to be fixed to a bone of said leg, such that at least the orientation of said leg can be determined by X-ray imaging of said bone.

11. A system according to claim 10, wherein said X-ray imaging is performed at two angles of rotation of said leg about its mechanical axis.

12. A system according to claim 11, wherein said X-ray imaging is performed by means of an X-ray imaging system and said mechanical axis of said leg is defined in the X-ray imaging system coordinate system.

13. A system according to claim 10, further comprising a cutting tool whose alignment is known relative to said bone, such that said cutting tool can cut said bone at a predetermined position relative to said mechanical axis of said leg.

14. A system according to claim 13, wherein said alignment of said cutting tool relative to said bone is known by means of attachment to said bone of a cutting jig for said cutting tool.

15. A system according to claim 13, wherein said alignment of said cutting tool relative to said bone is accomplished by a robot mounted in a known position relative to said bone, such that said predetermined position can be adjusted at least by means of programmed motion of said robot.

16. A system according to claim 9, wherein said leg rotation fixture is attached to an operating table, such that when the subject is on said operating table, said leg rotation fixture restricts movement of the leg to rotation about the mechanical axis of the leg.

\* \* \* \* \*